United States Patent [19]

Sanderson et al.

[11] Patent Number: 5,120,879

[45] Date of Patent: Jun. 9, 1992

[54] REACTION OF HYPOCHLORITES WITH POLYOXYPROPYLENE GLYCOLS

[75] Inventors: John R. Sanderson, Leander; Edward T. Marquis, Austin, both of Tex.

[73] Assignee: Texaco Chemical Company, White Plains, Tex.

[21] Appl. No.: 707,376

[22] Filed: May 30, 1991

Related U.S. Application Data

[63] Continuation-in-part of Ser. No. 583,101, Sep. 17, 1990, abandoned.

[51] Int. Cl.$^5$ ............................................. C07C 45/29
[52] U.S. Cl. ..................................... 568/405; 568/404
[58] Field of Search ............................. 508/405, 404

[56] References Cited

U.S. PATENT DOCUMENTS

| | | | |
|---|---|---|---|
| 3,479,403 | 11/1969 | MacLean | 200/530 |
| 4,233,460 | 11/1980 | Willis et al. | 562/537 |
| 4,256,916 | 3/1981 | Morris et al. | 562/537 |
| 4,488,944 | 12/1984 | Stutts et al. | 204/79 |
| 4,960,948 | 10/1990 | Sanderson et al. | 568/405 |
| 4,978,785 | 12/1990 | Sanderson et al. | 568/405 |
| 4,980,514 | 12/1990 | Sanderson et al. | 568/405 |

OTHER PUBLICATIONS

Anelli et al., J. Org. Chem., vol. 52, pp. 2559-2562 (1987).
Barak et al., J. Org. Chem., vol. 53, pp. 3553-3555 (1988).
Nishiguchi et al., J. Org. Chem., vol. 54, pp. 1531-1535 (1989).

*Primary Examiner*—James H. Reamer
*Attorney, Agent, or Firm*—Jack H. Park; Kenneth R. Priem; Carl G. Ries

[57] ABSTRACT

Polyoxypropylene diketones are prepared by initially adding predetermined amounts of a mono- or dicarboxylic acid having a pK < 4.5 and a water solubility at 25° C. of > 1%, a polyoxypropylene glycol and, optionally, water, to a reaction zone and thereafter adding an aqueous solution of an alkali metal or an alkaline earth metal hypochlorite oxidant to the reaction zone with agitation under reaction conditions including a temperature of about 10° to about 50° C., a pressure of about 0 to 1,000 psig. and a total reaction time of about 0.5 to 20 hours, whereby said polyoxypropylene glycol will be substantially selectively converted to the said corresponding diketone, and recovering said diketone.

7 Claims, No Drawings

REACTION OF HYPOCHLORITES WITH POLYOXYPROPYLENE GLYCOLS

RELATED APPLICATION

This application is a continuation-in-part of copending Sanderson and Marquis U.S. patent application Ser. No. 07/583,101, filed Sep. 17, 1990, now abandoned and entitled "Catalyzed Reaction of Hypochlorites with Polyoxypropylene Glycols".

BACKGROUND OF THE INVENTION

1. Technical Field of the Invention

This invention relates to the preparation of ketone derivatives of polyoxypropylene glycols. More particularly, this invention relates to a method wherein the terminal hydroxyl groups of a polyoxypropylene glycol are oxidized to ketone groups. Still more particularly, this invention is directed to a method wherein a polyoxypropylene glycol is brought into contact with a hypochlorite oxidant in the presence of a dicarboxylic acid having a pK <5, such salt having a water solubility >1%, in order to substantially selectively convert the terminal hydroxyl groups of the polyoxypropylene glycol to terminal ketone groups. The ketone terminated derivatives of polyoxypropylene glycols are useful as intermediates for the preparation of a wide variety of products. For example, they may be reacted with amines to provide fuel additives or converted to carboxylic acids to provide surfactants.

2. Prior Art

It is known to react secondary alcohols and primary benzyl and allyl alcohols to the corresponding ketones and aldehydes in the presence of an oxidant such as $Cu(NO_3)_2$ or $Zn(NO_3)_2$ supported on silica gel in the presence of an aliphatic hydrocarbon solvent or a chlorinated aliphatic hydrocarbon solvent as shown, for example, by a paper by Takeshi Nishiguchi and Fumi Asano entitled "Oxidation of Alcohols by Metallic Nitrates Supported on Silica Gel" (J. Org. Chem. 1989, 54, 1531-1535).

Willis et al. U.S. Pat. No. 4,233,460 discloses a process for converting alkoxyalkanols to the corresponding acids by reacting the alcohol with an alkali metal hydroxide and a tertiary butyl hydroperoxide in the presence of a catalytic amount of palladium. The oxidation of polyethylene glycols to dicarboxylic acids is disclosed by Morris et al. in U.S. Pat. No. 4,256,916 wherein it is disclosed that polyethylene glycols can be converted to the corresponding carboxylic acids by oxidation in an aqueous solution over a fixed bed of a catalyst consisting of platinum on a granular carbon support.

Stutts et al. U.S. Pat. No. 4,488,944 discloses the preparation of dicarboxylic acids by the oxidation of polyalkylene glycols with electrochemically generated nickeloxide hydroxide.

U.S. Pat. No. 3,479,403 to MacLean discloses that ruthenium can be used as an oxidation catalyst and that activity is enhanced by maintaining the oxidation potential of the ruthenium catalyst at less than the oxidizing potential of Ru(VIII) to greater than that of Ru(IV). In Example I, the oxidation of ethanol to acetic acid by the slow addition of an aqueous solution of calcium hypochlorite to an aqueous solution of ethanol containing a ruthenium chloride catalyst is disclosed. It is also disclosed in this example that the ruthenium chloride was oxidized to ruthenium tetraoxide. The oxidation of isopropanol to acetone with sodium hypochlorite in the presence of a ruthenium trichloride catalyst is also disclosed in Table II of the patent.

A method for the production of carboxylic acid derivatives and methyl ketone derivatives of polyoxypropylene glycols by the nitric acid oxidation of a polyoxypropylene glycol in the presence of an alkali metal nitrite is disclosed in Sanderson et al. U.S. Pat. No. 4,978,785.

Barak et al. in a paper entitled "Selective Oxidation of Alcohols by a $H_2O_2$—$RuCl_3$ System under Phase-Transfer Conditions" (J. Org. Chem., 1988, Vol. 53, pp. 3553-3555) discloses in part that secondary alcohols can be oxidized to ketones with one hundred percent selectivity when using hydrogen peroxide as the oxidizing agent. Wolfe et al. disclose in an article entitled "Ruthenium Trichloride-catalysed Hypochlorite Oxidation of Organic Compounds" (Chemical Communications, 1970, pp. 1420-1421) disclose that in the catalytic hypochlorite oxidation of organic compounds with ruthenium trichloride, the ruthenium trichloride is oxidized to ruthenium tetraoxide.

A paper entitled "Fast and Selective Oxidation of Primary Alcohols to Aldehydes or to Carboxylic Acids and of Secondary Alcohols to Ketones Mediated by Oxoammonium Salts under Two-Phase Conditions" by Anelli et al. (J. Org. Chem., 1987, Vol. 52, pp. 2559-2562) discloses oxidation of a variety of alcohols in solution in methylene chloride with sodium hypochlorite.

In all of the prior art references oxidation of polyoxyalkylene glycols has always been by oxidation of polyoxyethylene glycols. As far as we are aware, there are no references on the oxidation of a polyoxypropylene glycol to diketones. This is especially surprising in view of the fact that lower molecular weight secondary alcohols have been oxidized to ketones.

In copending Sanderson et al. U.S. application Ser. No. 07/444,211, filed Dec. 1, 1989, and entitled "Ketone Derivatives of Polyoxypropylene Glycols" (D#80,870), now U.S. Pat. No. 4,980,514 a process is disclosed wherein diketones are prepared by the oxidation of a polyoxypropylene glycol with an alkali metal or alkaline earth metal hypochlorite in the presence of a halogenated alkane solvent and a ruthenium catalyst.

SUMMARY OF THE INVENTION

In copending Sanderson et al. U. S. patent application Ser. No. 07/456,891, filed Dec. 26, 1989, and entitled "Manufacture of Ketone Derivatives of Polyoxypropylene Glycols", now U.S. Pat. No. 4,960,948, a process is disclosed wherein diketone derivatives of polyoxypropylene glycols are prepared by oxidizing the polyoxypropylene glycol with an alkali metal or alkaline earth metal hypochlorite in the presence of glacial acetic acid.

It has been surprisingly discovered in accordance with the present invention that a mono- or dicarboxylic acid having a pK <5 and a water solubility at 25° C. >1% unexpectedly functions as a catalyst when a polyoxypropylene glycol feedstock of the present invention is oxidized with an alkali metal or alkaline earth metal hypochlorite. It is not necessary to add another catalyst, such as a ruthenium catalyst.

It has been further discovered in accordance with the present invention that when only a catalytic amount of the carboxylic acid is used (about 5 to about 100 parts by weight of dicarboxylic acid reactant per 100 parts by weight of polyoxypropylene glycol), it is not necessary to use an extraneous solvent such as a halogenated alkane solvent.

In accordance with the present invention, a polyoxyproylene glycol having a molecular weight of about 200 to about 3,000 and having the formula:

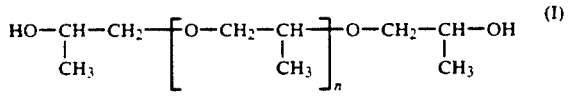

wherein n is a positive number having a value of 1 to about 50, is oxidized in the presence of a salt of a carboxylic acid having a pK <4.5 and a water solubility at 25° C. of >1% with an alkali metal or alkaline earth metal hypochlorite at a temperature of about 10° to about 50° C. and pressure of about 0 to 1,000 psig. over a period of about 0.5 to about 20 hours to provide a reaction product comprising the corresponding diketone having the formula:

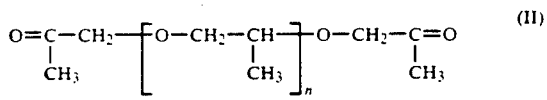

wherein n has the meaning given above.

The thus-prepared diketones are useful as intermediates for conversion to carboxylic acids to provide surfactants and for reaction with amine adducts to provide fuel additives, for example.

In accordance with a preferred embodiment of the present invention, a polyoxypropylene diketone having an average molecular weight of about 200 to about 3,000 is prepared by initially adding predetermined amounts of a polyoxypropylene glycol, a carboxylic acid having a pK <4.5 and a water solubility at 25° C. of >1% and, optionally, water, to a reaction zone and by continuously adding an aqueous solution of an alkali metal or an alkaline earth metal hypochlorite oxidant to the reaction zone with agitation under reaction conditions including a temperature of about 10° to about 50° C., a pressure of about 0 to 1,000 psig. and a total reaction time of about 0.5 to 20 hours, whereby the alkali metal or alkaline earth metal oxidant will react with the polyoxypropylene glycol to substantially selectively convert the polyoxypropylene glycol to the corresponding diketone, and recovering the diketone, the carboxylic acid being added in the ratio of about 5 to about 100 parts by weight of the carboxylic acid reactant per 100 parts by weight of said polyoxypropylene glycol, the water, when added, being added in the ratio of about 5 to about 100 parts by weight of water per 100 parts of polyoxypropylene glycol and in the ratio of about 1 to about 3 parts of water per part of the carboxylic acid reactant, the aqueous solution of the hypochlorite containing from about 5 to about 25 wt.% of the alkali metal or alkaline earth metal hypochlorite and being slowly added to the reaction zone over a period of time of about 0.5 to 5 hours in an amount within the range from about 10 to about 100 parts by weight of the hypochlorite per 100 parts by weight of the polyoxypropylene glycol.

DESCRIPTION OF THE PROCESS OF THE PRESENT INVENTION

The starting materials for the present invention include a polyoxypropylene glycol, as hereinafter defined, a mono- or dicarboxylic acid reactant having a pK <4.5 and a water solubility at 25° C. of >1%, an alkali metal or alkaline earth metal hypochlorite and, optionally, a minor amount of water.

The polyoxypropylene glycol feedstock to be used in accordance with the present invention is a polyoxypropylene glycol having an average molecular weight of about 200 to about 3,000 and having the formula:

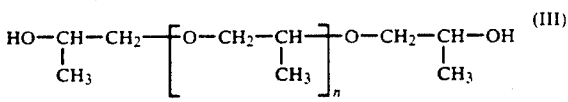

wherein n is a positive integer having a value of 1 to about 50.

The polyoxypropylene glycol feedstocks of the present invention are prepared commercially by reacting an initiator such as propylene glycol with an amount of propylene oxide sufficient to provide a polyoxypropylene glycol of the desired molecular weight. Since the addition of the propylene oxide is random, the final propoxylation product will not be a pure compound but, rather, will be a mixture of polyoxypropylene glycols. For example, if the amount of propylene oxide that is used is adequate to provide for a polyoxypropylene glycol having an average molecular weight of about 1,000, the final propoxylation product will actually be composed of a mixture of polyoxypropylene glycols having molecular weights varying from about 800 to about 1,200, the molecular weight distribution following a Gaussian distribution curve (sometimes referred to as a sine curve or a Poissan curve). As the average molecular weight of the polyoxypropylene glycol increases, the spread in molecular weight will also increase. Thus, when the average molecular weight of the polyoxypropylene glycol is 3,000, the deviation will be about 400 molecular weight units so that most of the product will fall within the molecular weight range of about 2,600 to about 3,400.

Also, the final propoxylation product will contain a minor amount of impurities (normally 5 wt.% or less) resulting, for example, from dehydration of terminal hydroxypropyl end groups which can occur to a limited extent at the reaction temperatures used during the propoxylation. A small portion of the feedstock will contain hydroxyethyl end groups.

Representative products of this nature include, for example, a polyoxypropylene glycol manufactured and sold by Texaco Chemical Company having an average molecular weight of about 230 (PPG-230), a polyoxypropylene glycol having an average molecular weight of about 400 (PPG-400) sold by the Texaco Chemical Company and a polyoxypropylene glycol having an average molecular weight of about 2,000 (PPG-2000) sold by the Texaco Chemical Company.

A mono- or dicarboxylic acid having a pK <4.5 and a water solubility at 25° C. of >1% is used to catalyze the reaction in accordance with the present invention. Representative mono- and dicarboxylic acids that may be used include benzoic acid, 3-chlorobenzoic acid, 4-chlorobenzoic acid, glycolic acid, oxalic acid, etc.

The oxidant to be used in accordance with the present invention is an alkali metal or alkaline earth metal hypochlorite such as sodium hypochlorite, calcium hypochlorite, potassium hypochlorite, etc.

The hypochlorite oxidant is preferably employed in the form of 5 to 25 wt.% aqueous solution of the hypochlorite.

The Reaction Procedure

The reaction procedure to be used in practicing the process of the present invention is a procedure wherein the polyoxypropylene glycol, the carboxylic acid, and water, if any, are added to a suitable reaction vessel, such as an autoclave, provided with appropriate agitation means and means for controlling temperature within the autoclave such as a jacket through which a heat exchange fluid may be circulated.

The hypochlorite oxidant is preferably employed in the form of 5 to 25 wt.% aqueous solution of the hypochlorite.

In practicing the process of the present invention, the polyoxypropylene glycol, and water, if any, are initially added to a reaction zone and thereafter the aqueous solution of alkali metal or alkaline earth metal hypochlorite oxidant is slowly added to the reaction zone with agitation.

The reaction conditions to be employed include a temperature of about 10° to about 50° C. (and more preferably about 10° to about 30° C.), a pressure of about 0 to 1,000 psig. (preferably autogenous pressure) and a reaction time of about 0.5 to 20 hours, and more preferably about 0.5 to about 5 hours.

The oxidation reaction will be about 80-90% complete at the end of the hypochlorite addition period, which will normally require from about 2 to about 5 hours, but since the oxidation reaction is a second order reaction, it will normally require about 15 to 20 hours of reaction at the indicated reaction temperature in order to bring the oxidation reaction to completion.

In general, the carboxylic acid should be added to the reaction zone in the ratio of about 5 to about 100 parts by weight of the carboxylic acid per 100 parts by weight of the polyoxypropylene glycol.

When water is added, the water should be added in the ratio of about 5 to about 100 parts by weight of water per 100 parts of polyoxypropylene glycol and in the ratio of about 1 to about 3 parts of water per part of the carboxylic acid reactant.

The aqueous solution of alkali metal or alkaline earth metal hypochlorite should preferably contain from about 5 to about 25 wt.% of hypochlorite and the amount of the aqueous solution of the hypochlorite slowly added to said reaction zone should be an amount such that from about 10 to about 100 parts of hypochlorite is added to the reaction zone per 100 parts by weight of said polyoxypropylene glycol, and more preferably in the ratio of about 20 to about 50 parts by weight of hypochlorite per 100 parts of polyoxypropylene glycol.

At the end of the reaction, the polyoxypropylene diketone may be recovered from the reaction mixture in any suitable manner, such as by solvent extraction (e.g., solvent extraction with a chlorinated alkane such as trichlorethane, by extractive distillation, etc.

As a result, the polyoxypropylene glycol feedstock will be substantially selectively converted to the corresponding diketone derivative having the formula:

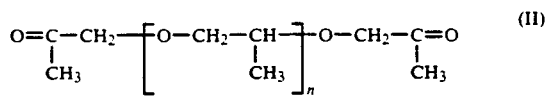

wherein n is a positive number having a value of 1 to about 50.

As indicated, the polyoxypropylene glycol feedstock comprises a mixture of polyoxypropylene glycols and minor amounts of other impurities. Thus, for example, although 95 wt.% or more of the polyoxypropylene glycol feedstock will contain terminal hydroxypropyl end groups that are substantially selectively oxidized to ketone end groups when using the process of the present invention, the feedstock will contain a small amount of feed components having terminal hydroxyethyl end groups. The hydroxyethyl end groups will normally be oxidized to carboxylic acid groups.

Also, the methylene group adjacent an ether group is susceptible to limited oxidation, i.e.

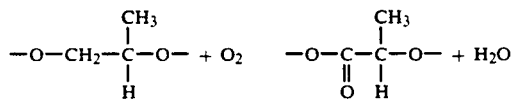

SPECIFIC EXAMPLES

The invention will be further illustrated by the following specific examples which are given by way of illustration and not as limitations on the scope of this invention.

Use of Glacial Acetic Acid as a Solvent

Procedure

Polyoxypropylene glycol-2000 (Hydroxyl No. 56.0) and a predetermined amount of a mono- or dicarboxylic acid were charged to a flask equipped with stirrer, water bath, thermometer, condenser and addition funnel. Sodium hypochlorite (10%) was added dropwise over 0.5-2.0 hours. There was a mild exotherm but the temperature was maintained at 20°-25° C. by means of a water/ice bath. The reaction mixture was stirred for an additional 15 hours at 20°-25° C. The mixture was then poured into water and the product extracted with 1,1,1-trichloroethane. The trichlorethane was extracted 5% NaHCO3 water. The organic solution was then dried over sodium sulfate and the solvent removed on a rotary evaporator.

The mono- and dicarboxylic acids that were used, the quantities of reactants, the reaction conditions and the results obtained are summarized in Table I.

TABLE I

| | OXIDATION OF POLYPROPYLENE GLYCOL 2000 WITH SODIUM HYPOCHLORITE CATALYZED BY CERTAIN ORGANIC ACIDS[a] | | | | | | | | | | |
|---|---|---|---|---|---|---|---|---|---|---|---|
| | PPG-2000 | 10% NaOCl | | | | | Reaction | | Hydroxyl | Acid | |
| Notebook Number | (g) | (g) | Solvent | (g) | Acid | (g) | Time (Hr) | Temp. (°C.) | Number meg/g | No. meg/g | H2O % |
| 6528-15 | 50 | 100 | 1,1,1-Tri- | 100 | 3-chloro- | 8.0 | 16 | 20-25 | 8.63 | 0.90 | 0.031 |

TABLE I-continued

OXIDATION OF POLYPROPYLENE GLYCOL 2000 WITH SODIUM HYPOCHLORITE CATALYZED BY CERTAIN ORGANIC ACIDS[a]

| Notebook Number | PPG-2000 (g) | 10% NaOCl (g) | Solvent | (g) | Acid | (g) | Reaction Time (Hr) | Reaction Temp. (°C.) | Hydroxyl Number meq/g | Acid No. meq/g | H₂O % |
|---|---|---|---|---|---|---|---|---|---|---|---|
| 6528-21 | 100 | 250 | chloroethane None | — | benzoic acid Benzoic acid | 12.0 | 2 | 20–45 | 49.2 | 3.95 | 0.060 |
| 6528-22 | 100 | 250 | None | — | Glycolic acid | 10.0 | 2 | 20–40 | 25.0 | 1.03 | 0.044 |
| 6528-25 | 100 | 250 | None | — | Pivalic acid | 10.0 | 4 | 20–35 | 47.1 | 2.34 | 0.060 |
| 6528-26 | 100 | 250 | None | — | Oxalic acid | 3.0 | 4 | 20–25 | 22.2 | — | 0.031 |
| 6528-27 | 100 | 250 | None | — | Benzoic acid | 2.5 | 20 | 20–25 | 25.4 | — | 0.010 |
| 6528-35 | 200 | 600 | None | — | Citric acid | 5.0 | 25 | 20–25 | 58.6 | 0.95 | 0.020 |
| 6528-39 | 100 | 250 | None | — | Phenyl Phosphonic acid | 5.0 | 18 | 20–25 | 47.4 | 2.02 | 0.030 |
| 6528-65 | 200 | 600 | None | — | 4-chlorobenzoic acid | 10.0 | 15 | 20–25 | 23.5 | 6.59 | 0.119 |
| 6528-58 | 200 | 600 | None | — | None | — | 16 | 20–25 | 55.4 | 0.36 | 0.026 |

[a]PPG-2000 has OH No. of 56.0 mg/g

Satisfactory results were obtained for Run No. 6528-15, Run No. 6528-22, Run No. 6528-26, Run No. 6528-27, and Run No. 6528-65, as evidenced by the comparatively low hydroxyl numbers of the reaction products as compared with the hydroxyl number of the reaction product of Run No. 6528-68, where the hydroxyl number of the reaction product was 55.4. Unsatisfactory results were obtained in Run No. 6528-21, Run No. 6528-25, Run No. 6528-35, Run No. 6528-39, and control experiment Run No. 6528-58.

The different results obtained in Run No. 6528-21 and Run No. 6528-27 are not completely understood, and it appears that the adverse results reported for Run No. 6528-21 may be the result of poor mixing.

Adverse results were obtained in Run No. 6528-25 because pivalic acid is a comparatively weak acid having a pK of 5.05. Although citric acid has a pK of 3.13, adverse results were obtained because citric acid is a known oxidation inhibitor. Although phenyl phosphoric acid has a pK of 1.86, it does not have a solubility in water of >1% at 25° C.

Having thus described our invention, what is claimed is:

1. A method of making a polyoxypropylene diketone having an average molecular weight of about 200 to about 3,000 which comprises:
adding predetermined amounts of a carboxylic acid having a pK <4.5 and a water solubility at 25° C. of >1%, a polyoxypropylene glycol and, optionally, water, to a reaction zone and thereafter adding an aqueous solution of an alkali metal or an alkaline earth metal hypochlorite oxidant to the reaction zone with agitation under reaction conditions including a temperature of about 10° to about 50° C., a pressure of about 0 to 1,000 psig. and a total reaction time of about 0.5 to 20 hours, whereby said oxidant will react with said polyoxypropylene glycol and substantially selectively convert said polyoxypropylene glycol to the said corresponding diketone, and recovering said diketone,
said carboxylic acid being selected from the group consisting of benzoic acid, chloro-substituted benzoic acids, oxalic acid and glycolic acid,
said carboxylic acid being added in the ratio of about 5 to about 100 parts by weight of said carboxylic acid per 100 parts by weight of said polyoxypropylene glycol,
said water, when added, being added in the ratio of about 5 to about 100 parts by weight of water per part 100 parts by weight of polyoxypropylene glycol and in the ratio of about 1 to about 3 parts of water per part of said carboxylic acid,
said aqueous solution of said hypochlorite containing from about 5 to about 25 wt.% of said hypochlorite and being slowly added to said reaction zone over a period of about 0.5 to 5 hours in an amount of from about 10 to about 100 parts by weight of said hypochlorite per 100 parts by weight of said polyoxypropylene glycol,
said polyoxypropylene diketone having the formula:

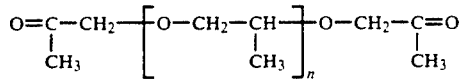

wherein n represents a positive number having a value of 1 to about 50.

2. A method as in claim 1 wherein the hypochlorite is an alkali metal hypochlorite.

3. A method as in claim 2 wherein the alkali metal hypochlorite is sodium hypochlorite.

4. A method as in claim 3 wherein the said carboxylic acid is selected from the group consisting of benzoic acid, 3-chlorobenzoic acid, 4-chlorobenzoic acid, glycolic acid and oxalic acid.

5. A method as in claim 4 wherein the polyoxypropylene glycol added to the reaction zone is a polyoxypropylene glycol having an average molecular weight of about 2000 and wherein n in the formula of claim 1 represents a number having an average value of about 33.

6. A method of making a polyoxypropylene diketone having an average molecular weight of about 200 to about 3,000 which consists of:
adding predetermined amounts of a carboxylic acid, a polyoxypropylene glycol and water, to a reaction zone and thereafter adding an aqueous solution of sodium hypochlorite to the reaction zone with agitation under reaction conditions including a temperature of about 10° to about 30° C., atmospheric pressure and a total reaction time of about 0.5 to 5 hours, whereby said sodium hypochlorite will react with said polyoxypropylene glycol and substantially selectively convert to said corresponding diketone, and recovering said diketone, said carboxylic acid reactant having a pK <4.5, a water solubility at 25° C. of >1%, and being selected from the group consisting of benzoic acid, chloro-substituted benzoic acids, oxalic acid and glycolic acid, said carboxylic acid being added in the ratio of about 5 to about 100 parts by weight of said carboxylic acid per 100 parts by weight of said polyoxypropylene glycol, said water being added in the ratio of about 30 to about 50 parts by weight of water per 100 parts by weight of polyoxypropylene glycol and in the ratio of about 1 to about 3 parts of water per part of said carboxylic acid, said aqueous solution of said hypochlorite containing from about 5 to about 25 wt.% of said hypochlorite and being slowly added to said reaction zone over a period of about 1 to about 3 hours in an amount of from about 20 to about 50 parts by weight of said hypochlorite per 100 parts by weight of said polyoxypropylene glycol, said polyoxypropylene diketone having the formula:

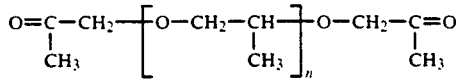

wherein n in said formula represents a positive number having a value of 1 to about 50.

7. A method as in claim 6 wherein the polyoxypropylene glycol added to the reaction zone is a polyoxypropylene glycol having an average molecular weight of about 2,000 and wherein n in the formula of claim 10 represents a number having an average value of about 33.

* * * * *